(12) United States Patent
Esfandyarpour et al.

(10) Patent No.: US 8,696,989 B2
(45) Date of Patent: Apr. 15, 2014

(54) CALORIMETER SENSOR

(75) Inventors: Hesaam Esfandyarpour, Los Altos, CA (US); Ronald W. Davis, Palo Alto, CA (US)

(73) Assignee: The Board of Trustees of the Leland Stanford Junior Univerity, Palo Alto, CA (US)

( * ) Notice: Subject to any disclaimer, the term of this patent is extended or adjusted under 35 U.S.C. 154(b) by 0 days.

(21) Appl. No.: 13/481,363

(22) Filed: May 25, 2012

(65) Prior Publication Data

US 2013/0029851 A1 Jan. 31, 2013

Related U.S. Application Data

(60) Provisional application No. 61/491,054, filed on May 27, 2011.

(51) Int. Cl.
G01N 25/20 (2006.01)
G01K 17/00 (2006.01)
G01K 17/08 (2006.01)
C12Q 1/68 (2006.01)

(52) U.S. Cl.
USPC .................. 422/51; 374/10; 374/31; 435/6.1

(58) Field of Classification Search
USPC ................. 422/51; 435/6.1; 436/147; 506/33
See application file for complete search history.

(56) References Cited

U.S. PATENT DOCUMENTS 7,932,034 B2   4/2011  Esfandyarpour et al.
2008/0166727 A1*  7/2008  Esfandyarpour et al. ......... 435/6

OTHER PUBLICATIONS

Adrega et al., "Chip calorimeter for thermal characterization of biochemical solutions," Sensors and Actuators A: Physical 2011, 167:354-358, published online Mar. 21, 2011.*
H. Esfandyarpour and R.W. Davis, "Gate-Controlled Microfluidic Chamber with magnetic bead for DNA Sequencing-by-synthesis Technology", ICNMM2007, ref-30119, pp. 1-5 (2007).
H. Esfandyarpour, B. Zheng, R.F.W. Pease, and R.W. Davis, "Structural optimization for heat detection of DNA thermosequencing platform using finite element analysis," J. of Biomicrofluidics, vol. 2, pp. 024102-1-024102-11 (2008).
H. Esfandyarpour and R.W. Davis. "An Integrated Differential Nanocalimeter with On-Chip Microfluidic Multiplexing for High Throughput Genomics and Proteomics." 14$^{th}$ Int'l Conf. on Miniaturized Systems for Chem. And Life Sciences, 3 pgs. Groningen, the Netherlands (Oct. 3-7, 2010).

(Continued)

*Primary Examiner* — Samuel Woolwine
*Assistant Examiner* — Kaijiang Zhang
(74) *Attorney, Agent, or Firm* — Crawford Maunu PLLC

(57) ABSTRACT

A calorimeter device includes various components located on a common substrate. A first (calorimeter) integrated chip device is located on the substrate. This first device has a first microfluidic channel that has first side and a second side. A first heat sensing circuit is located on the first side of the first channel and a second heat sensing circuit is located on the second side of the channel, opposite the first side and facing the first heat sensing circuit. A second integrated chip device is located on the substrate and proximal to the first device. The second device includes a second microfluidic channel having a third side and fourth side. A third heat sensing circuit is located on the third side of the second channel. A fourth heat sensing circuit is located on the fourth side of the channel, opposite the third side and facing the third heat sensing circuit.

18 Claims, 12 Drawing Sheets

(56) References Cited

OTHER PUBLICATIONS

H. Esfandyarpour and R.W. Davis. "Integrated Differential Silicon Nano-Calorimeter with on-chip Microfluidic for Real-Time High-Throughput Drug Discovery." MicroTas Conference 2010, 2 pgs. Groningen, the Netherlands (Jun. 1-4, 2010).

H. Esfandyarpour. "Electronic gene sequencing [electronic resource]: a novel method for DNA sequencing based on direct heat or pH measurement." Stanford University, Thesis, Special Collection Archives. Call No. 3781 2010 E., Chapt. 4 (p. 30-42), Chapt. 6 (p. 51-64), and Chapt. 7 (p. 65-119).

W. Lee et al. "High-sensitivity microfluidic calorimeters for biological and chemical applications." PNAS, vol. 106, No. 36, p. 15225-15230 (Sep. 8, 2009).

E. Iervolino et al. "Calorimeter chip calibration for thermal characterization of liquid samples." Thermochimica Acta 492, p. 95-100 (May 3, 2009).

T. Adrega and A. W. van Herwaarden. "Chip Calorimeter for Thermal Characterization of Bio-Chemical Solutions." Sensors and Actuators A: Physical. vol. 167, No. 2, 13 pgs. (Mar. 21, 2011).

\* cited by examiner $\Delta T = T - T_{amb} = P/G_{total}$

CALORIMETER SENSOR

RELATED DOCUMENTS

This patent document claims benefit under 35 U.S.C. §119 of U.S. Provisional Patent Application Ser. No. 61/491,054 entitled "Calorimeter Sensor" and filed on May 27, 2011; this patent document and the Appendices filed in the underlying provisional application, including the references cited therein, are fully incorporated herein by reference.

FEDERALLY-SPONSORED RESEARCH AND DEVELOPMENT

This invention was made with Government Support under contract HG000205 awarded by the National Institutes of Health. The Government has certain rights in this invention.

FIELD

The present disclosure is directed to apparatuses and methods involving measurement of heat.

OVERVIEW

Aspects of the present disclosure relate to a method and calorimeter sensor for the measurement of heat produced by a chemical reaction. In one or more embodiments, an on-chip integrated microfluidic calorimeter with differential and dual-sided sensor architecture is presented. This architecture dramatically improves the signal to noise ratio and reduces the common noise and calibration issues.

Various embodiments of the present disclosure relate to applications that involve measurement of heat. For example, the disclosed method and sensors are thought to be applicable to a fast and label-free DNA sequencing method called "thermosequencing," which can potentially reduce the cost of sequencing. The method and sensor are also thought to be applicable to a wide variety of other biomedical processes including metabolic activities of microorganisms, living cells, catalyzed reactions, etc. While the present disclosure is not necessarily limited in these contexts, various aspects of the disclosure may be appreciated through a discussion of examples using these and other contexts.

As discussed in more detail herein, high sensitivity microfluidic calorimeters can be useful for achieving high throughput, inexpensive, and fast biomedical measurements with low sample consumption. High sensitivity and precise injections and calibrations limitations, however, can be major issues for such devices. Aspects of the present disclosure include description of design, fabrication and testing and optimization of an on-chip integrated microfluidic calorimeters, some of which can be useful for addressing these and other issues. Particular embodiments are directed toward on-chip integrated microfluidic calorimeters with differential and/or dual-sided sensor architecture. Various related embodiments have been found particularly useful for addressing problems relating to signal to noise ratio, the common noise and calibration.

As also discussed herein, calorimeter devices can be constructed from several integrated circuits (ICs), each of which can be placed in a single package and/or on the same unifying substrate (e.g., a ceramic of glass substrate for ease of integration with sample sources). Integrated circuits or monolithic integrated circuits (also referred to as ICs, or chips) include one or more electronic circuits manufactured onto the surface of a thin substrate of semiconductor material. Multiple integrated circuits can be placed in a single multi-chip module (MCM), which can function as a single component.

Various aspects of the present disclosure are directed toward a method and calorimeter sensor useful for measuring heat produced by a chemical reaction, such as from DNA sequencing. Various other possibilities exist, some of which are discussed in more detail herein and as supported in the underlying provisional application 61/491,054 entitled "Calorimeter Sensor" and filed on May 27, 2011, which includes the Appendices filed therein, and which is fully incorporated herein by reference.

SUMMARY

Aspects of the present disclosure relate generally to interfaces and methods relating to the applications discussed above.

Embodiments of the present disclosure are directed toward a semiconductor chip-based microfluidic calorimeter. The calorimeter includes a number of different features that can be used alone or in combination to facilitate the calorimeter readings for nanoliter-scale sample sizes and in real time.

Embodiments of the present disclosure are directed toward a method of measuring heat generated in a chemical reaction. Two different samples are provided to a microfluidic channel of an on-chip calorimeter. Heat that is generated from a reaction between the first and second samples is then monitored using two thermosensors of the calorimeter. The two thermosensors are positioned on opposite sides of the microfluidic channel facing one another.

Consistent with certain embodiments, a calorimeter sensor is constructed with various components located on a common substrate. A first (calorimeter) integrated chip device is located on the substrate. This first device has a first microfluidic channel that has a first side and a second side. A first heat sensing circuit is located on the first side of the first channel and a second heat sensing circuit is located on the second side of the channel, opposite the first side and facing the first heat sensing circuit. A second integrated chip device is located on the substrate and proximal to the first device. The second device includes a second microfluidic channel having a third side and a fourth side. A third heat sensing circuit is located on the third side of the second channel. A fourth heat sensing circuit is located on the fourth side of the channel, opposite the third side and facing the third heat sensing circuit.

The above summary is not intended to describe each embodiment or every implementation of the present disclosure. The figures, detailed description and claims that follow more particularly exemplify various embodiments.

BRIEF DESCRIPTION OF THE DRAWINGS

Aspects of the present disclosure may be more completely understood in consideration of the detailed description of various embodiments of the present disclosure that follows in connection with the accompanying drawings, in which.

Figure 1:
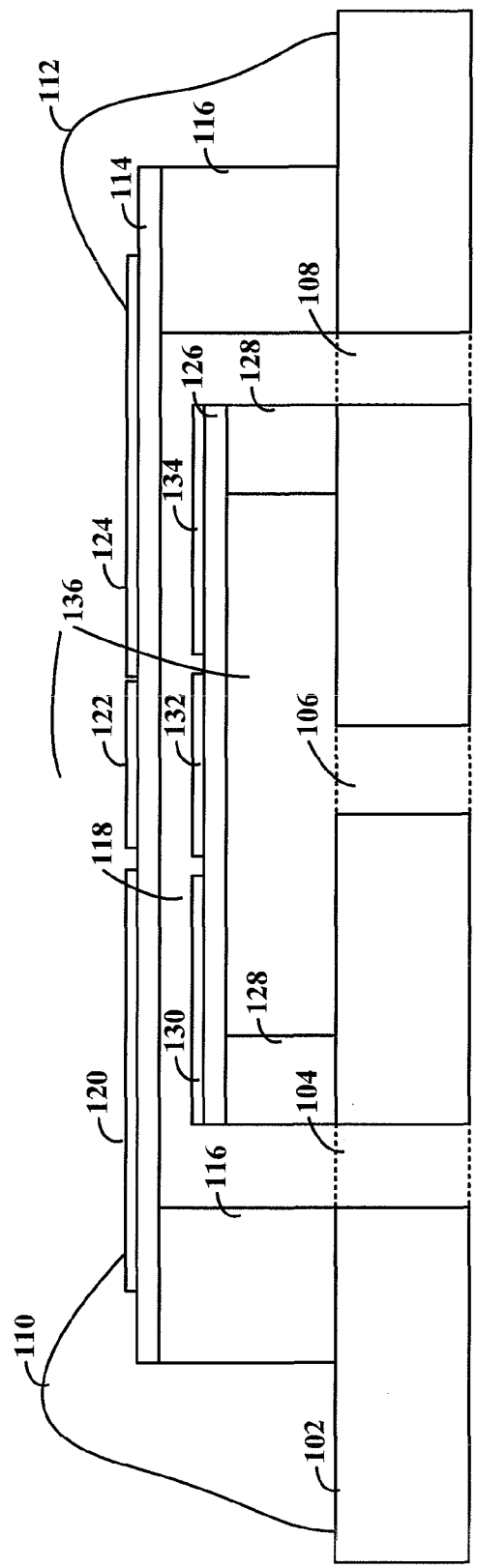
FIG. 1 depicts a diagram of an on-chip calorimeter device, consistent with embodiments of the present disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION

The present disclosure relates to devices for on-chip calorimeters, to methods of using on-chip calorimeters and to methods of manufacturing on-chip calorimeters. While the present disclosure is not necessarily limited to such devices and applications, various aspects of the disclosure may be appreciated through a discussion of examples using these and other contexts.

Embodiments of the present disclosure are directed toward a semiconductor chip-based microfluidic calorimeter. The calorimeters can be designed for detection of chemical reactions on the nanoliter-scale while providing real-time readings. For instance, such calorimeters can be used to characterize a wide variety of the biomedical processes, such as metabolic activities of microorganisms, living cells and catalyzed reactions. In another instance, the calorimeters can be used in a fast and label-free DNA sequencing method sometimes referred to as "DNA thermosequencing." Accordingly, certain embodiments are directed toward on-chip sequential injection and an associated multiplexing unit, which can be useful for sequential injection of different nucleotides into the integrated microfluidic calorimeter device for DNA thermosequencing. Certain experimental embodiments of the present disclosure have shown the surprising capability of being able to characterize the heat of a reaction with 2-nW resolution in nanoliter-scale sample sizes and in real time.

Certain embodiments are directed toward aspects of sample delivery to an on-chip reaction. For instance, sample injection can be carried out using an on-chip Polydimethylsiloxane (PDMS) Multiplexing microfluidic unit that is interfaced to one or more microfluidic calorimeter integrated circuit chips. Such a unit can be particularly useful for providing the precise sequential injection of sub-nanoliter. Various example embodiments relating to the design and fabrication of microfluidic multiplexing modules for precise serial injection are discussed in more detail herein.

Embodiments of the present disclosure are directed toward a method of measuring heat generated in a chemical reaction. Two different samples are provided to a microfluidic channel of an on-chip calorimeter. Heat that is generated from a reaction between the first and second samples is then monitored using two thermosensors of the calorimeter. The two thermosensors are positioned on opposite sides of the microfluidic channel facing one another. Surprisingly, problems that might be expected from the added complexity of multiple sensors in the small integrated circuit environment (e.g., mechanical integrity, signal crosstalk, thermal crosstalk and others) have been overcome through careful design and experimentation or, to the extent they were not overcome, they were found to have been outweighed by the benefits provided by the additional sensor.

It has been recognized that embodiments of the present disclosure are scalable to highly multiplexed, automated array architectures. The array-based architecture of such devices can be particularly useful for high throughput, low cost and sample volume measurements for screening of large analyte libraries in a short time. In addition, an on-chip microfluidic-multiplexing unit can be useful for precise sequential injection having minimal dead volume and for high throughput genomics, proteomics and drug development.

Various embodiments of the present disclosure are directed toward the use of a second reference calorimeter. This second reference calorimeter can be configured to include the same arrangement of components as the first calorimeter. Various sources of undesirable degradation of signal/measurement quality can be compensated for using this second reference calorimeter. For instance noise (e.g., electrical or thermal), disturbances from sample manipulation and injection, manufacturing variances and other sources of signal integrity issues are often seen by both the first calorimeter and the second reference calorimeter. Signal readings from the second reference calorimeter can therefore be used as a baseline from which to develop a filter for removing undesired interference. For instance, by not introducing the sample under test to the second reference calorimeter, measurements from the microfluidic channel of a reference calorimeter are compared against those from the first calorimeter. The differential between these two measurements represents the result of the reaction or sample that is under test without the undesired interference. Thus, heat absorbed by the first calorimeter can be determined by comparing temperature readings of the first calorimeter's two opposing thermosensors to temperature readings from the two opposing thermosensors of the second reference calorimeter. In certain instances, the effectiveness of such a differential calorimeter can be facilitated by placing the two calorimeters in close proximity and adjacent to one another. Consistent with certain embodiments, an amount of heat determined to have been absorbed by the microfluidic channel of the first mentioned calorimeter can be compensated for by adding a proportional amount of the heat.

As discussed in more detail herein, the first and second thermosensors can be implemented using a variety of different sensor types, and these sensor types can be used in combination or in isolation. Consistent with a particular embodiment, the thermosensors are constructed on a membrane that defines the microfluidic cavity. These thermosensors can be constructed using voltage differentials created by junctions between two dissimilar conductors or metals (the "Seebeck effect"). A more specific embodiment is directed toward thermosensors that are constructed from a plurality of p- and n-doped polysilicon thermocouples. Such thermocouples can also include a polysilicon heater and the components can be arranged in what is sometimes referred to as a thermopile. Consistent with certain embodiments the membranes are constructed from SiN.

Embodiments of the present disclosure recognize that the efficiency of thermocoupling between material in the microfluidic channel and the thermosensors can be improved by providing a small separation distance. Accordingly, the first and second thermosensors are separated by no more than 1 mm for embodiments of the present disclosure. In other embodiments, the separation can be set to be no more than 300 µm.

Other aspects of the present disclosure are directed toward how the first and second samples are delivered to the microfluidic channel of the calorimeter. For instance, the samples can be delivered by injecting a controlled volume of the first and second samples into the microfluidic channel by sequentially closing adjacent valves to facilitate peristaltic pumping of the first and second samples.

Consistent with certain embodiments, a calorimeter sensor is constructed with various components located on a common substrate. A first (calorimeter) integrated chip device is located on the substrate. This first device has a first microfluidic channel that has a first side and a second side. A first heat sensing circuit is located on the first side of the first channel and a second heat sensing circuit is located on the second side of the channel, opposite the first side and facing the first heat sensing circuit. A second integrated chip device is located on the substrate and proximal to the first device. The second device includes a second microfluidic channel having a third side and fourth side. A third heat sensing circuit is located on the third side of the second channel. A fourth heat sensing circuit is located on the fourth side of the channel, opposite the third side and facing the third heat sensing circuit.

Consistent with certain embodiments, the first and second sides (as well as the third and fourth sides) are separated by no more than 1 mm. In other embodiments, the sides are separated by no more than 300 µm. Other separations are also possible. In a particular embodiment, each integrated chip device is a silicon (Si) chip and each side is a silicon nitride (SiN) membrane. It is also possible that the SiN membranes are separated from external heat sources by either an air gap or a vacuum gap.

The calorimeter sensor can also include, or be in communication with, circuitry that is configured and arranged to filter first data that is received from the sensors of the first device. This filtering can include a differential comparison of the first data to second data that is received from the sensors of the second device.

As discussed herein, the calorimeter sensor can be configured to perform DNA thermosequencing. Accordingly, the calorimeter sensor can be configured to further include a plurality of beads encapsulated in the first channel, wherein each bead is coated with a plurality of DNA strands.

Turning now to the figures, FIG. 1 depicts a diagram of an on-chip calorimeter device, consistent with embodiments of the present disclosure. The various components are located on a substrate 102. The substrate can be made out of various different materials depending upon the particular application. For instance, the use of ceramic or glass substrate can be useful for providing a functional interface with external sample sources. Thus, the substrate can include holes 104, 106, 108 at corresponding location for inlet(s) (104), outlet(s) (106) and vacuum encapsulation input (108). In certain embodiments, the substrate 102 can include electrical conductors that provide input, output and power to integrated circuit(s) located on the substrate 102. As a non-limiting example, such electrical conductors can be linked to the integrated circuit by way of bond wires 110, 112.

Membrane 114 extends over and helps form a first side (laterally-extending) of a microfluidic channel 118. This suspended membrane 114 is supported, on each end of the microfluidic channel 118, by support structures 116 (e.g., a semiconductor layer or substrate configured to interface with another structure to form microfluidic channel 118). In particular embodiments, these support structures 116 can be constructed from silicon (Si) material and the membrane 114 can be constructed from a silicon nitride (SiN) material. The membrane 114 also includes thermosensors 120, 124. In various embodiments, it can also be beneficial to include a heat generating element 122. For instance, the combination of the thermosensors 120, 124 and heat generating element 122 can form a thermopile, or an array of thermocouples.

Membrane 126 extends under and helps form a second side (laterally-extending) of the microfluidic channel 118. This suspended membrane 126 is supported, on each end of the microfluidic channel 118, by support structures 128. In particular embodiments, these support structures 128 can be constructed from silicon (Si) material and the membrane 126 can be constructed from a silicon nitride (SiN) material. The membrane 126 also includes thermosensors 130, 134.

In various embodiments, it can also be beneficial to include a heat generating element 132. In certain embodiments, the heat generating element is a thin film resistor. This thin film resistor can act as an on-chip heater for calibration of the calorimeter device; this resistor can also be used as thermistor or thermal resistive sensor. For instance, the combination of the thermosensors 130, 134 and heat generating element 132 can form a thermopile, or an array of thermocouples.

Each thermocouple can include of two dissimilar metals connected in series and laying parallel to one another. One end of the thermocouple is kept at a constant "cold" temperature, while the heat generating element 122 (e.g., resistive element) warms the other end. When subjected to a temperature gradient, a conductor will generate a voltage, known as the Seebeck effect; different metals will form different voltages depending on their Seebeck coefficients or $dV=\alpha_s dT$.

A larger difference in Seebeck coefficients gives rise to a larger signal, while longer lengths of the conductors increase sensitivity, particularly if suspended over a membrane. The metals can be constructed using thin film laid over a substrate, or using doped silicon. Depending on the metal used, they can be compatible with typical CMOS processes.

Table 1 lists few materials and their respective Seebeck factors while the junction Seebeck factor is the difference between the two materials $\alpha_s$. To have the maximum sensitivity, it is required to use the materials with higher Seebeck factors; thus in the integrated microfluidic calorimeter device, the thermocouple junctions are made of p- and n-doped polysilicon to result in a high Seebeck factor or $\alpha_s$, and thus sensitivity.

$$\alpha_s = \frac{mk}{q}\ln(\rho/\rho_0)$$

For instance, for n-p polysilicon thermopiles, $\rho_0 = 5e^{-6}$ and m=2.5 as constants, for a 0.4 urn thick with sheet resistance of 250-2500 ohm/square.

TABLE 1

Seebeck Factor of some materials in Thermopiles

| Material | Seebeck Coefficient (uV/K) |
|---|---|
| p-type Polysilicon | 300 |
| Chrome | 17.3 |
| Gold | 1.94 |
| Copper | 1.83 |
| Aluminum | −1.7 |
| Platinum | −5.28 |
| n-type Polysilicon | −350 |

For a thermopile, which is an array of thermocouple, usually connected in series, the sensitivity can be proportional to the number (N) of thermocouple junctions. On the other hand, increasing N in a constrained area results in thinner strips, which increases the resistance of the thermopile and corresponding noise. A suitable value for N can therefore be determined by:

$$N \cong \sqrt{\frac{R_{st}W}{R_{sc}L_x}}$$

where $R_{sc}$ is the (technology-dependent) electrical sheet resistance.

As a rule of thumb for an optimum N, the thermopiles stripes can be set to be at least as thick as the required separation between the strips; e.g., thermopile R can be set to be between 5 to 200 KΩ, not too high so as to reduce interference, and not too low so as to the influence of the offset from external circuits.

Each membrane 114, 126 can be thermally isolated from external heat sinks and sources by a gap 136. In certain instances, the gap is an air gap, in others the gap is a vacuum gap. For instance, vacuum encapsulation input (108) can be used to create a vacuum gap.

Consistent with various embodiments of the present disclosure, the lower membrane 126 and support structure 128 layer are aligned and fixed to the substrate 102 (e.g., by gluing to a ceramic (or glass) substrate). The alignment includes matching the holes at corresponding locations for inlets, an outlet and a vacuum encapsulation input. Then the second/top membrane 114 and support structure 116 is then aligned and glued to bottom structure. This combination creates the microfluidic chamber 118 between the two face-to-face membranes 114, 126. Consistent with other embodiments, the two membranes and support structures can be fixed to each other before being placed on the substrate 102.

Figure 2:
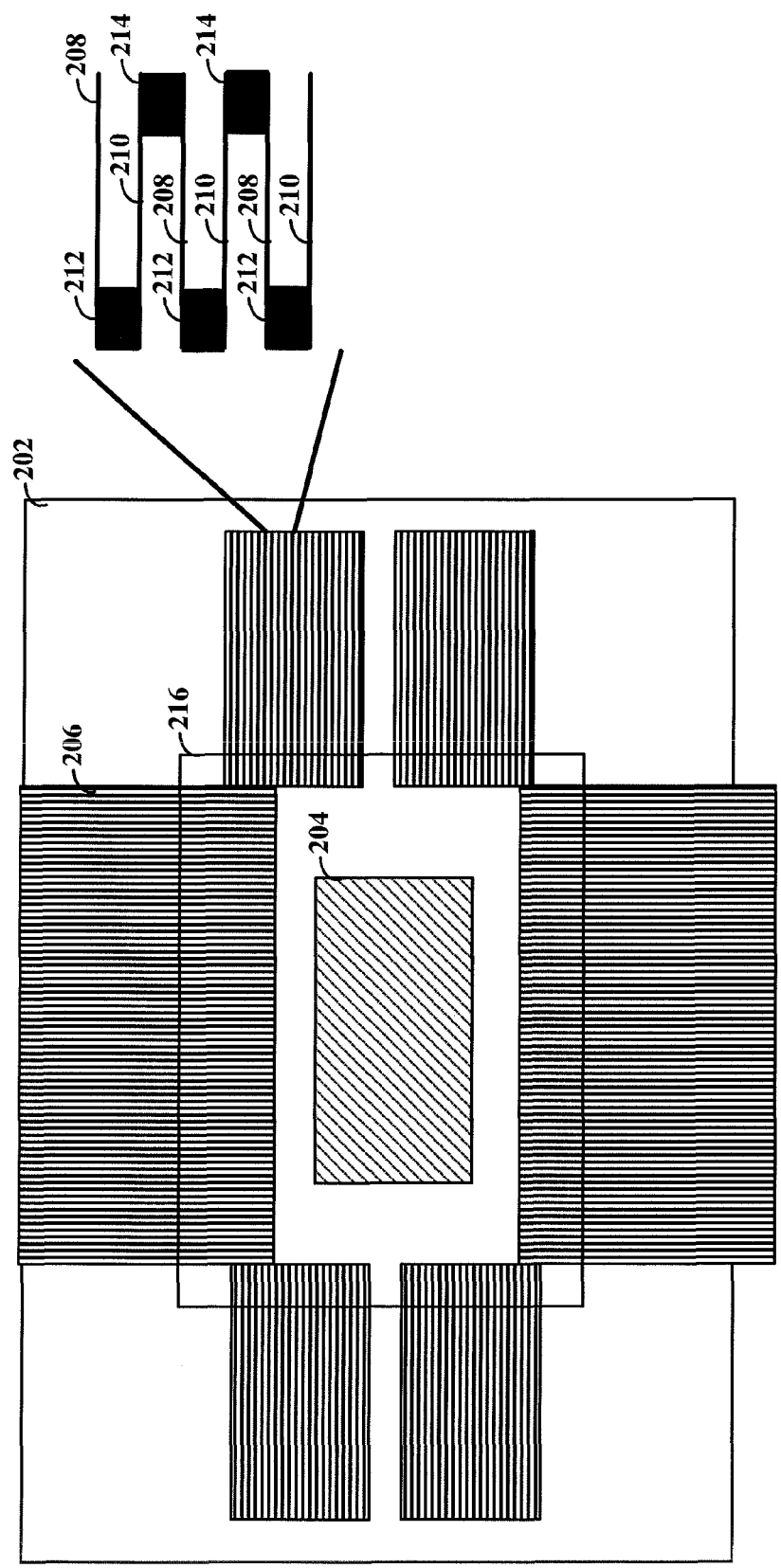
FIG. 2 depicts a top-down view of a top membrane, consistent with embodiments of the present disclosure.

FIG. 2 depicts a top-down view of a top membrane, consistent with embodiments of the present disclosure. The membrane 202 includes a heating element 204. In certain embodiments, this heating element can be constructed using one or more resistive elements that provide heat using an applied voltage/power. Such resistive elements can also be used as thermoresistors to detect temperature. Surrounding the heating element 204 is one or more thermosensors 206. In a particular embodiment, the thermosensors 206 are arranged to create a thermopile that can detect changes in temperature using the Seebeck effect.

A particular embodiment of thermosensors 206 is depicted in more detail by elements 208-214. Conductive strip 208 is constructed from a first material that has a first Seebeck coefficient. Conductive strip 210 is constructed from a second material that has a second, different Seebeck coefficient. Junction points 212, 214 provide voltage differentials that are based upon relative temperatures. Thus, a temperature difference between these junction points can be changed by heat being generated in reaction area, which would cause near junction points to be exposed to elevated temperatures. The reaction area can be within the area 216, which represents a suspended portion of the membrane 202 (e.g., a 1.6 um SiN thin film).

Figure 3:
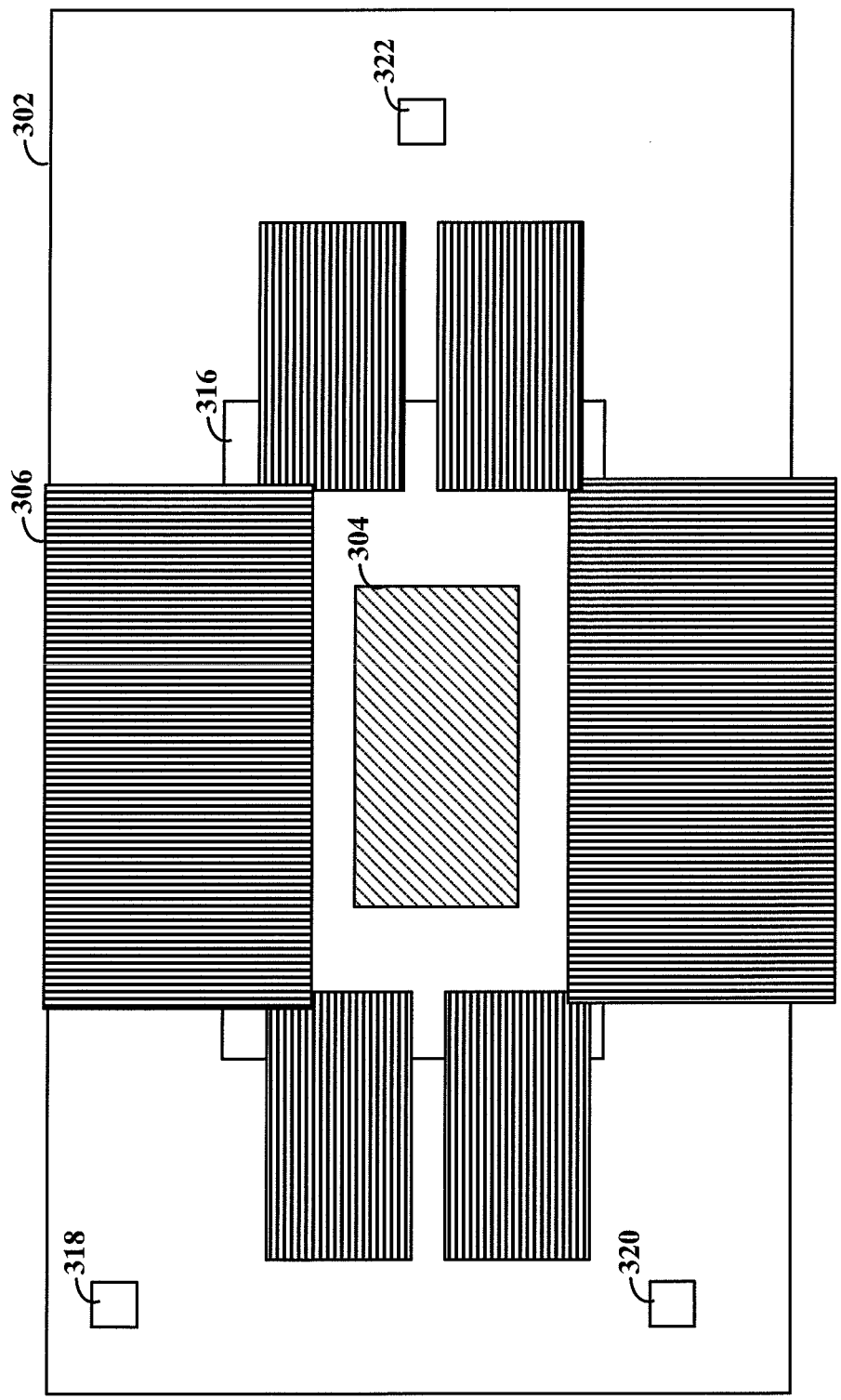
FIG. 3 depicts a bottom-up view of a bottom membrane, consistent with embodiments of the present disclosure.

FIG. 3 depicts a bottom-up view of a bottom membrane, consistent with embodiments of the present disclosure. The membrane 302 includes a heating element 304. In certain embodiments, this heating element can be constructed using one or more resistive elements that provide heat using an applied voltage/power. Such resistive elements can also be used as thermoresistors to detect temperature. Surrounding the heating element 304 is one or more thermosensors 306. In a particular embodiment, the thermosensors 306 are arranged to create a thermopile that can detect changes in temperature using the Seebeck effect. Thus, these thermosensors can be used to detect heat being generated in a reaction area. The reaction area can be within the area 316, which represents a suspended portion of the membrane 302 (e.g., a 1.6 μm SiN thin film).

Inlets 318 and 320 provide entry points from which two samples can be provided to the microfluidic channel created by membranes 202 and 302. Outlet 322 provides an exit point for such samples to leave the microfluidic channel. In other embodiments, the relationship between input and output can be reversed or additional ports can be added or removed.

Figure 4:
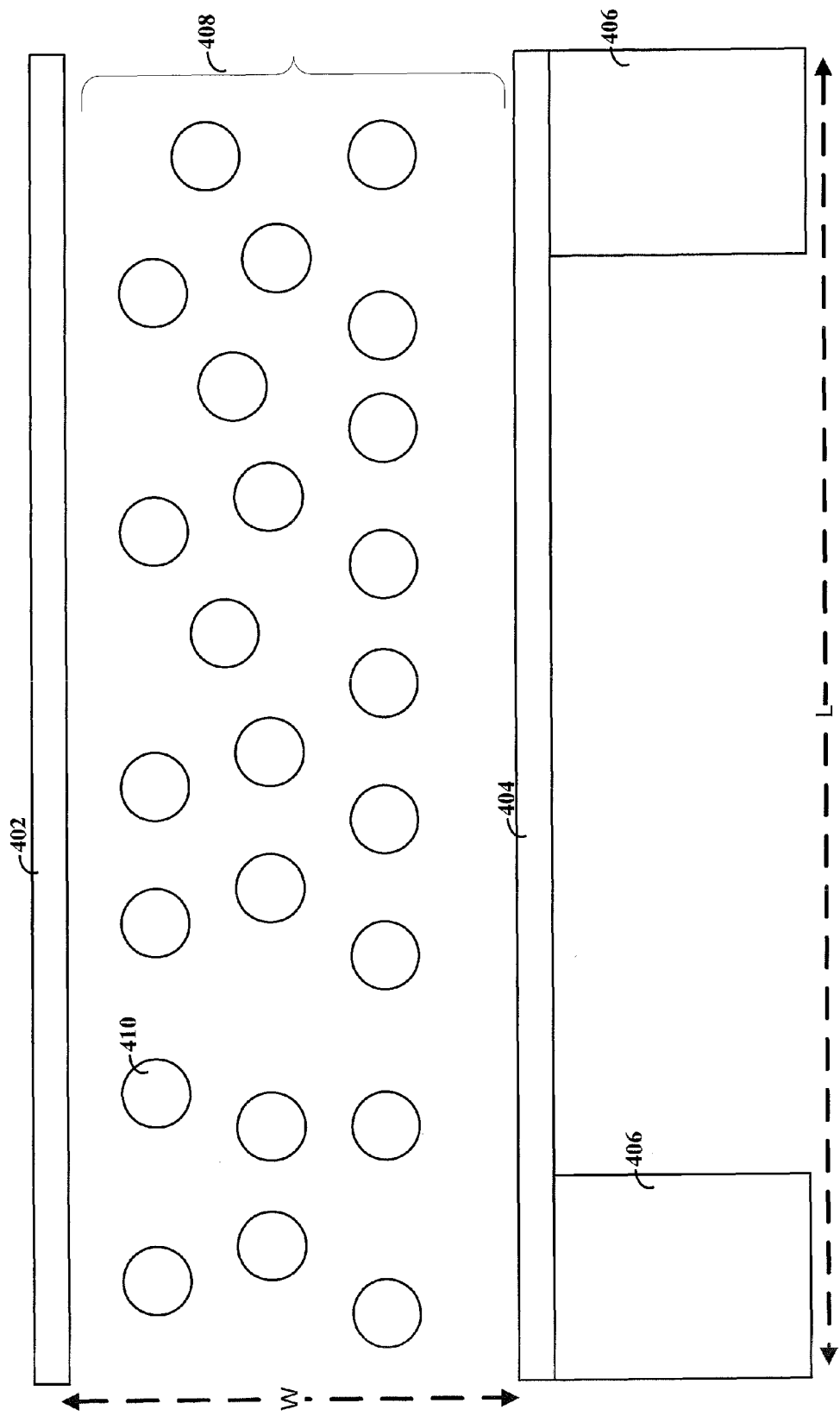
FIG. 4 depicts a microfluidic channel loaded with DNA-coated beads, consistent with embodiments of the present disclosure.

FIG. 4 depicts a microfluidic channel loaded with DNA-coated beads, consistent with embodiments of the present disclosure. Membranes 402 and 404 are located on opposite sides of microfluidic channel 408. As discussed herein, each of these membranes can include thermosensors that face one another and that extend in a lateral direction along the microfluidic channel 408. Support structures 406 support membrane 404. Support structures (not shown) also support membrane 402. The device depicted in FIG. 4 also includes a plurality of beads 410. Each of these beads 410 can have numerous DNA strands affixed thereto. For instance, the beads 410 can be small (e.g., 2.8 μm) magnetic beads in a solution. DNA molecules can then be introduced to the solution. The resulting DNA-coated beads are then encapsulated in the reaction chamber of the microfluidic channel 408. Such a configuration can be particularly useful for performance of DNA thermosequencing.

For example, multiple sequential injections of four different types of nucleotide solution can be presented to the chamber (e.g., dATP, dTTP, dCTP, dGTP). Measured heat can be used to determine whether or not a reaction occurred with the DNA molecules. A buffer washing step can then be performed between the injections.

Such a thermosequencing method relies on the detection of released heat from DNA synthesis. The equation for DNA synthesis is:

$$DNA_n + dNTP \xrightarrow{polymerase} DNA_{n+1} + PPi + \Delta H$$

$\Delta H = -12.8$ KCal/mol $= -0.507$ ev/base molecule

The formula represents the incorporation of a nucleotide, dNTP, which could be any nucleotide, G: Guanine, A:

Adenine, T: Thymine, or C: Cytosine incorporated into a growing DNA strand. The ΔH in the above reaction is about 22 kT or ~570 meV per nucleotide incorporation. The incorporation of the nucleotide in the above reaction is monitored to provide sequence information.

As described herein, for thermal isolation, the calorimeter can be designed on two thin film membranes, suspended in air or vacuum. In addition, to increase the thermal isolation, capturing more of the released energy from reactions, and another independent readout signal from the same reaction, a thermopile array on each thin film layer (top and bottom) can be used.

Figure 5:
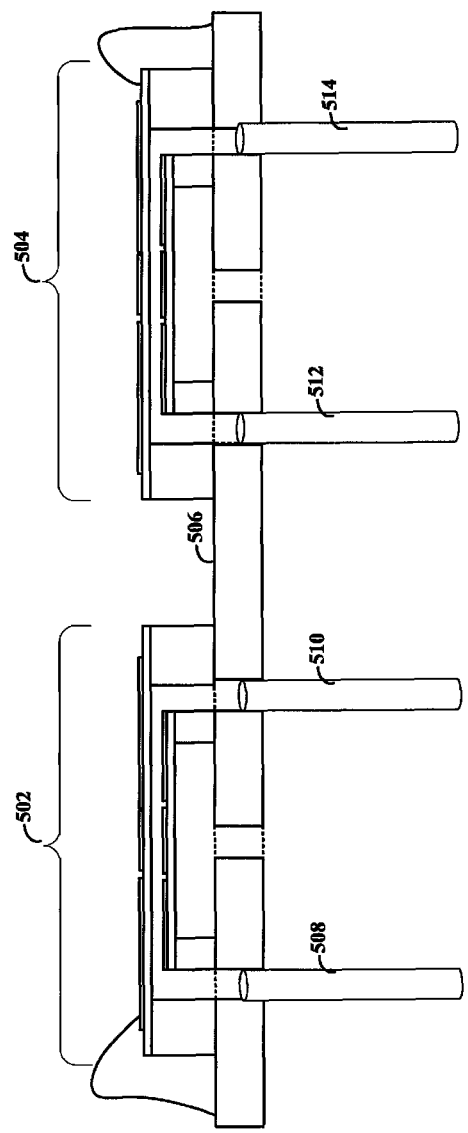
FIG. 5 depicts a differential-measurement architecture or solution, consistent with embodiments of the present disclosure.

FIG. 5 depicts a differential-measurement architecture or solution, consistent with embodiments of the present disclosure. This differential-measurement architecture of microfluidic calorimeter can be used to compensate for common noise and disturbance due to, among other things, temperature fluctuation, thermal noise, fluidic injection, mixing and other sources of noise. Ideally, two calorimeter devices 502, 504 are virtually identical and embedded close to each other. In operation, they will be used to take measurements in a similar fashion, however, only one of devices is subjected to the real chemical reaction (e.g., DNA sequencing polymerization) while the other device acts as a reference device.

Consistent with embodiments of the present disclosure, the two integrated circuit devices 502, 504 are placed on a common substrate 506. In many embodiments, these two integrated circuit devices 502, 504 are as close to identical as possible. This can include, for instance, being constructed with the same materials and to the same dimensions. Moreover, these two integrated circuit devices 502, 504 can be manufactured from a common wafer using the same manufacturing process. Thus, although manufacturing processes and wafer materials may vary slightly between different production runs, the integrated circuit devices 502, 504 can be selected from a common wafer and manufacturing run.

The integrated circuit devices 502, 504 can also be placed in close proximity to one another. This can be particularly useful for ensuring that the devices are subjected to very similar temperature fluctuation and/or other noise that may be affected by spatial displacement between the integrated circuit device 502, 504.

For instance, one or more samples can be introduced to the integrated circuit device 502 using inlet 508, 512 and outlet 510, 514. At the same time, a buffer solution, that does not contain the chemically active portion of the sample being test, is introduced to integrated circuit device 504. The temperature readings from each of the integrated circuit devices 502, 504 should differ primarily based upon any heat generated by a reaction caused by the sample introduced to the integrated circuit device 502. Accordingly, noise received at both integrated circuit devices 502, 504 can be filtered out (e.g., by taking a differential of the two signals).

Consistent with certain embodiments, a more sophisticated filtering process can be undertaken. For example, a calibration process can be undertaken to detect differences between the integrated circuit devices 502, 504. This can be particularly useful to allow for adjustments based upon non-idealities of the two integrated circuit devices 502, 504. This can include, but is not necessarily limited to, sensitivity or gain of the thermosensors, time-based offsets and relative susceptibility to noise. The filter can be adjusted to compensate for such differences. In some instances, the differences may be non-linear and can therefore be approximated by a polynomial function of the appropriate degree.

Figure 6:
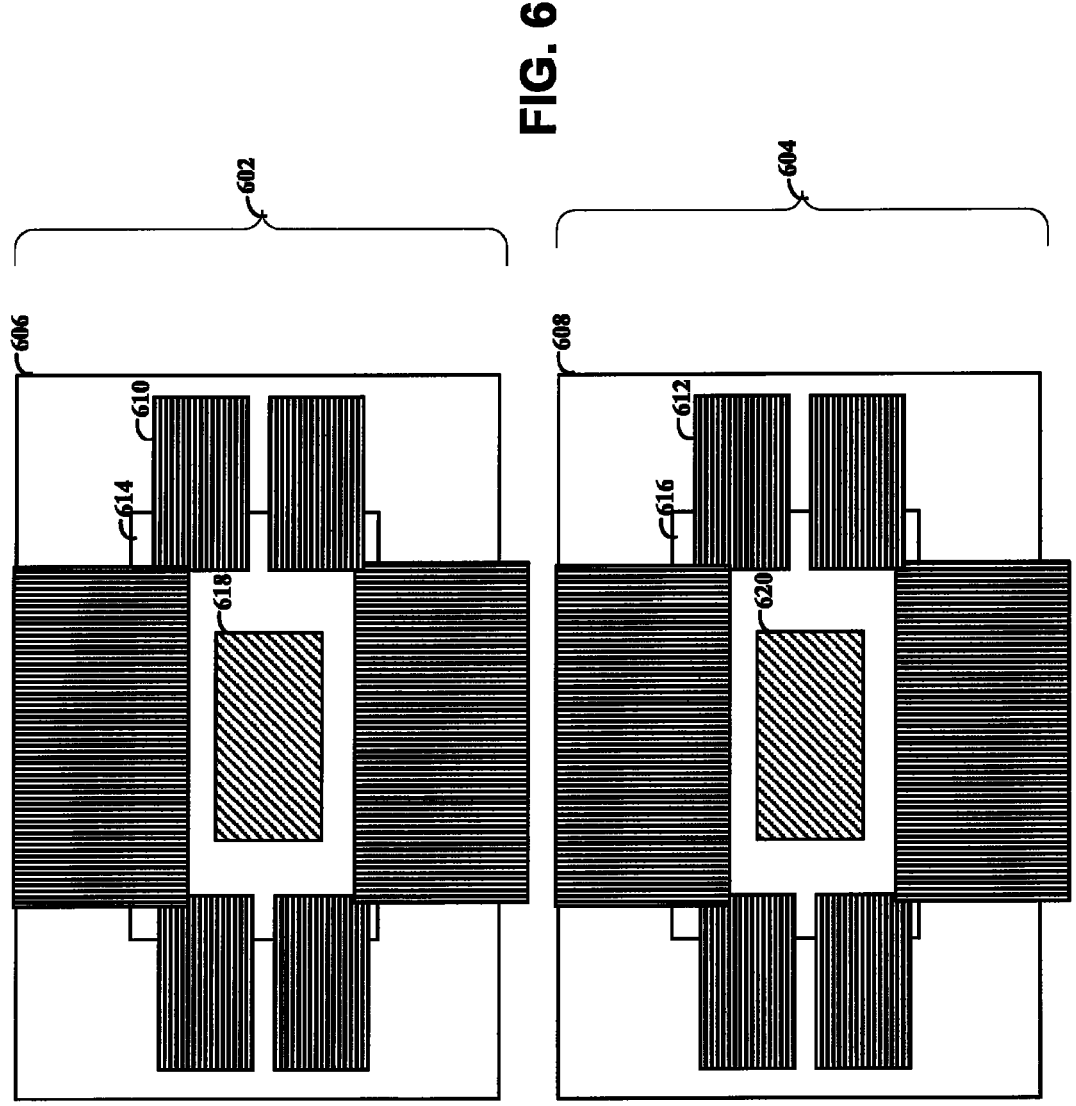
FIG. 6 depicts a top-down view of a set of differentially configured integrated circuit devices, consistent with embodiments of the present disclosure.

FIG. 6 depicts a top-down view of a set of differentially configured integrated circuit devices, consistent with embodiments of the present disclosure. As discussed herein, the integrated circuit devices 602, 604 can be constructed so as to be as close to identical as possible. This includes, for instance, the relative parameters for one or more of the membranes 606, 608; thermocouples 610, 612; suspended portions of the membrane 614, 616; and heating elements 618, 620.

Figure 7:
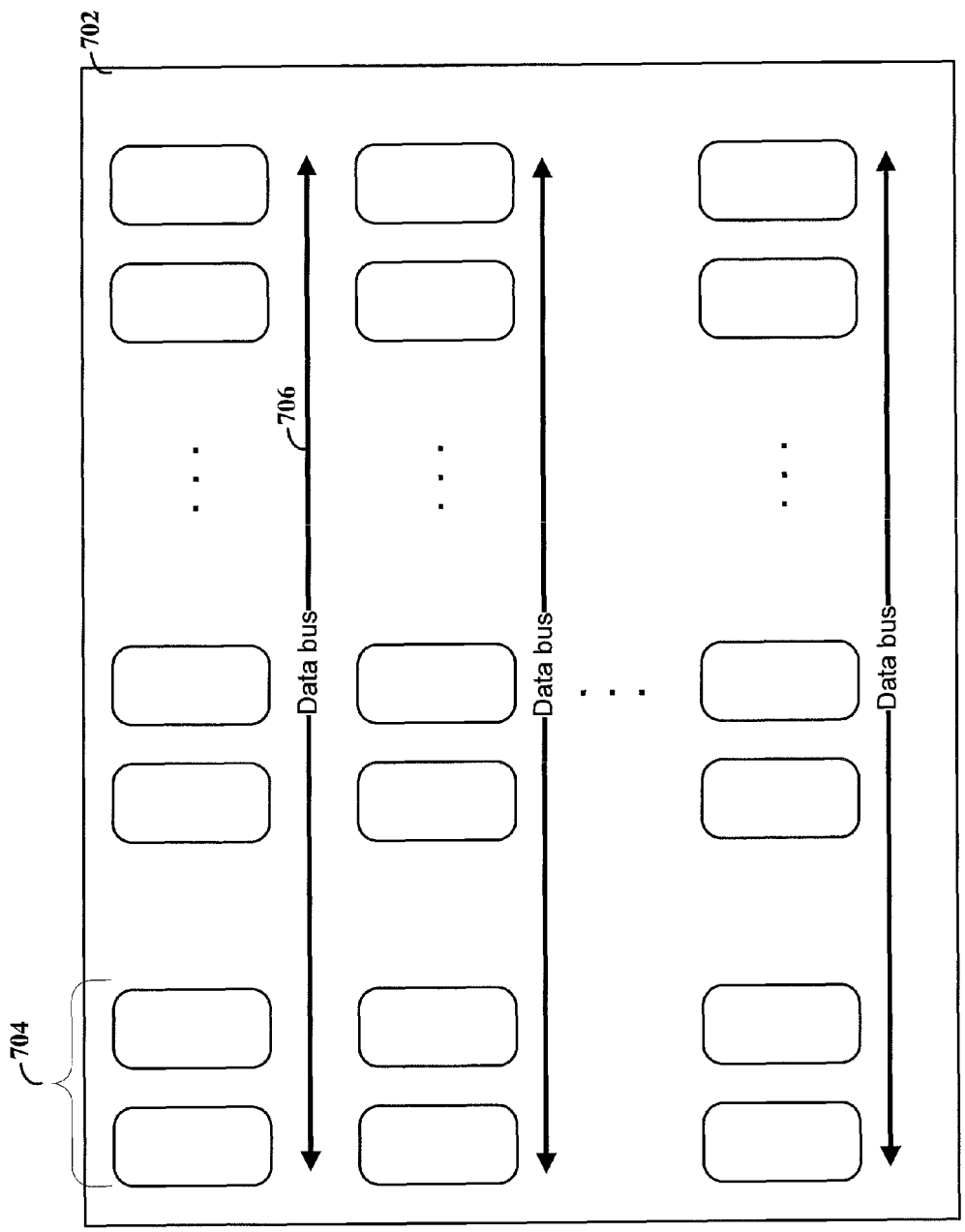
FIG. 7 depicts an array-based architecture for differential calorimeters, consistent with embodiments of the present disclosure.

FIG. 7 depicts an array-based architecture for differential calorimeters, consistent with embodiments of the present disclosure. As discussed herein, such an array-based architecture can be particularly useful for high throughput, low cost and sample volume measurements for screening of large analyte libraries in a short time. A base or substrate 702 provides support for a plurality of differential integrated circuit device pairs 704. Each device pair 704 can be configured to perform a respective calorimeter measurement allowing for many different measurements to be carried out in parallel. Thus, the various device pairs can perform measurements of respective and different samples, reactions and the like. Alternatively, a common set of measurements can be carried out for similar or identical samples, reactions and the like (e.g., to provide a higher confidence level of the results).

One or more data busses 706 can be used to retrieve sensor data from the differential integrated circuit device pairs 704. The data busses 706 can also be used to provide control signals for PDMS Multiplexing or for a heating element. Alternatively, one or more control logic circuits can be co-located on the substrate 702 to add additional intelligence to the architecture (e.g., to provide local signal filtering and amplification).

Figure 8:
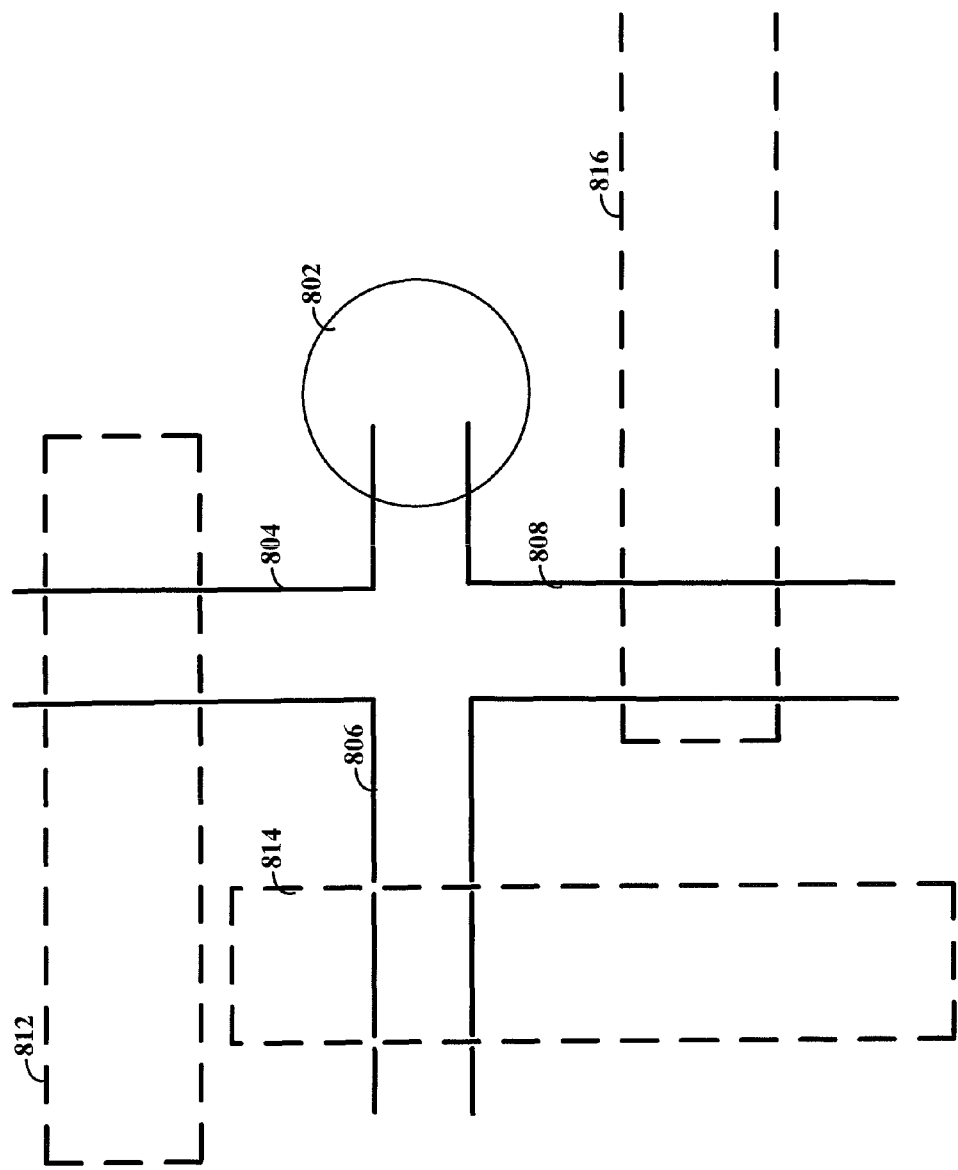
FIG. 8 depicts a delivery system that is based upon a PDMS Multiplexed solution, consistent with embodiments of the present disclosure.

FIG. 8 depicts a delivery system that is based upon a PDMS Multiplexed solution, consistent with embodiments of the present disclosure. For a precise and repeatable serial injection of liquid substance into the microfluidic calorimeter, it can be important to be able to precisely control the amount of sample injected to the device as well to be able to switch between different reservoirs during sequential injections. FIG. 8 depicts an inlet (or outlet) 802, which provides a fluid path to the microfluidic channel of the calorimeter. Multiple distinct input channels 804, 806, 808 are linked to the inlet 802. Control channels 812, 814, 816 cross over respective and corresponding input channels 804, 806, 808. The control channels 812, 814, 816 are controllable to close off their corresponding input channels 804, 806, 808.

Consistent with particular embodiments, multistep soft-lithography is used to create PDMS channels 804, 806, 808 and valves can readily provide an automated, precise, multiplex and sequential injection with minimal dead-volume. The flow and control channels 812, 814, 816 are also part of the Microfluidic Multiplex unit, which is made in PDMS. These control channels can be aligned and bound to a ceramic (or glass) substrate/interface, which interfaces with micro fluidic chamber's inlets/outlet. The PDMS-to-ceramic (-to-calorimeter microfluidic inlets) interface can be particularly useful for facilitating integration of calorimeter functions with other forms of lab-on-a-chip devices for precise multiplexed sequential injection. Expansion of control channels (e.g., using pressure) causes the input channels 804, 806, 808 to be closed.

Consistent with various embodiments, each inlet and outlet of the calorimeter can be connected to four injection flow lines with corresponding control lines. Alternate numbers of lines per inlet and outlet are also possible.

Embodiments of the present disclosure are also directed toward the recognition of a problem of errors in readout of microfluidic based sensors that are caused by the creation of a bubble in the channel, especially where such a bubble reaches the reaction chamber. This can make an accurate measurement impractical since even minute movements of the bubble, relative to the sensor, can create undesirable effects on the measured signal. Aspects of the present disclosure are directed toward mitigating such a bubbling issue for the detection of one specific reaction (e.g., specific protein binding or catalyzed (Urea) detection) by using intermediate sample reservoirs tubes. The whole integrated on-chip microfluidic calorimeter system can then be located and tested in a closed metallic box, as a Faraday Cage to minimize the 60-Hz and other noises disturbing the detection. The ionized solution in the tubes connected to the syringe and pump (outside the box) can transfer some of the O-Hz and other noise sources to the output signal. In addition to eliminating the bubble, such a configuration can help to reduce the 60-Hz noise seen inside of the "Faraday Cage."

Moreover, it is recognized that the low dead-volume for reagents and samples can reduce the cost of operation of the calorimeter device. In addition to precise and accurate sequential injection, the microfluidic injection system can be more easily used in an automated platform.

Consistent with particular embodiments of the present disclosure, a PDMS multiplexing unit's architecture is provided that allows variable control of the sample injection volume by sequentially closing three adjacent PDMS valves to facilitate peristaltic pumping. The control channels can be ~100 um wide whereas the flow channels can be ~10 um wide. Each valve permits reproducible injection of a 500 pL fluidic volume with ≈30 pL accuracy. The overall operational protocol of the calorimeter can be modified readily by replacing the PDMS microfluidic system with a variety of alternative designs.

Figure 9:
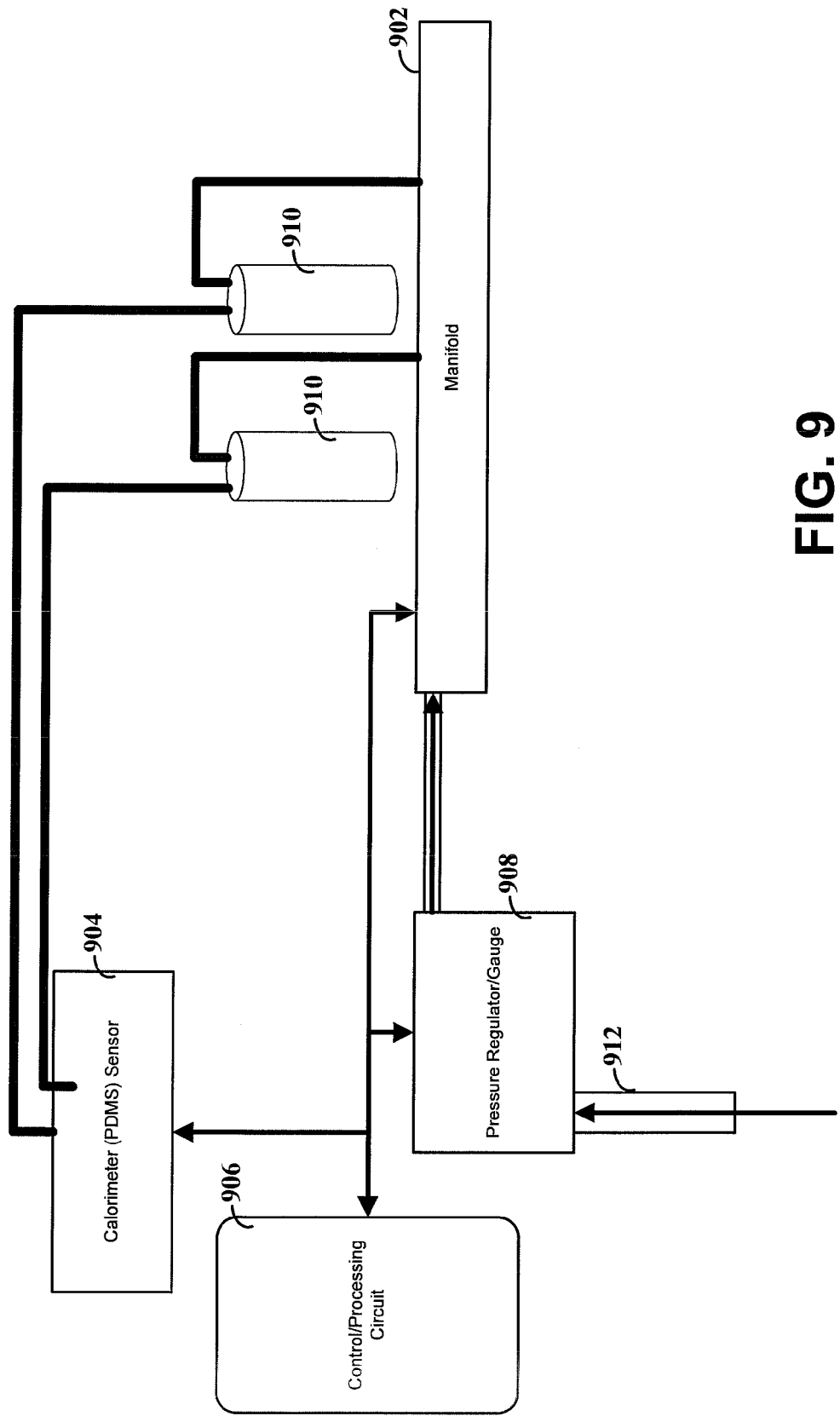
FIG. 9 depicts a platform and system for switching an injection with an electronic valve controller, consistent with embodiments of the present disclosure.

FIG. 9 depicts a platform and system for switching an injection with an electronic valve controller, consistent with embodiments of the present disclosure. The sequential multiplexing microfluidics can benefit from high-speed switches (Manifold 902, PDMS switches 904) that provide fast gating of the channel, thus the precise pico-liter injection of the samples between reservoirs 910 and the integrated microfluidic calorimeter. Accordingly, an array of valve-controller switches can be linked to a high-speed processing/control unit 906. For instance, the processing unit could be implemented on a specially-designed circuit or using a personal computer running specially-configured software (Labview or MATLAB software with appropriate programming) and an appropriate signaling interface, such as USB. One or more pressure regulators 908 can be used to regulate the air pressure before passing through the manifolds 902. The air pressure can be provided from a pressure source 912, which can then be regulated and monitored using the pressure regulators 908.

Figure 10:
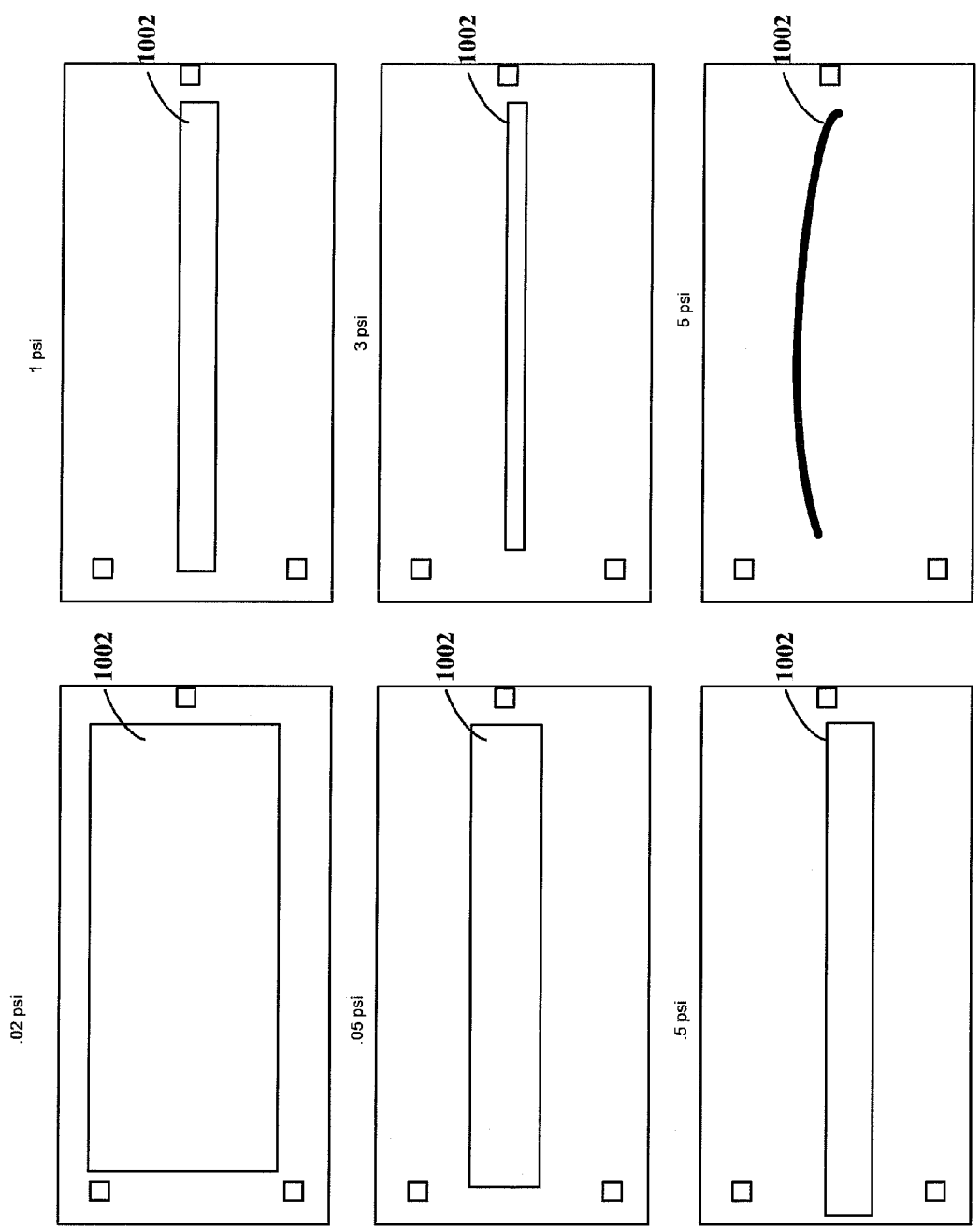
FIG. 10 depicts the effective mixing reaction area 1002 for six different injection flow rates (e.g., pressures) based upon experimental tests and consistent with embodiments of the present disclosure.

In certain embodiments, the volume of mixing region or the "real reaction chamber" varies when two samples involved in the reaction are injected from the two inlets, e.g., depending on the flow rate of injection and diffusion constants. For two specific samples in a reaction (e.g., Urea and Urease), this volume is directly proportional to injection flow rates and diffusion constants. The larger mixing volume corresponds to larger energy release and hence it directly influences the detection limit or sensitivity of the calorimeter device. On the other hand, sensitivity would be directly proportional to the number of active thermocouple sensors present in the mixing area. Accordingly, FIG. 10 depicts the effective mixing reaction area 1002 for six different injection flow rates (e.g., pressures) based upon experimental tests and consistent with embodiments of the present disclosure.

Figure 11:
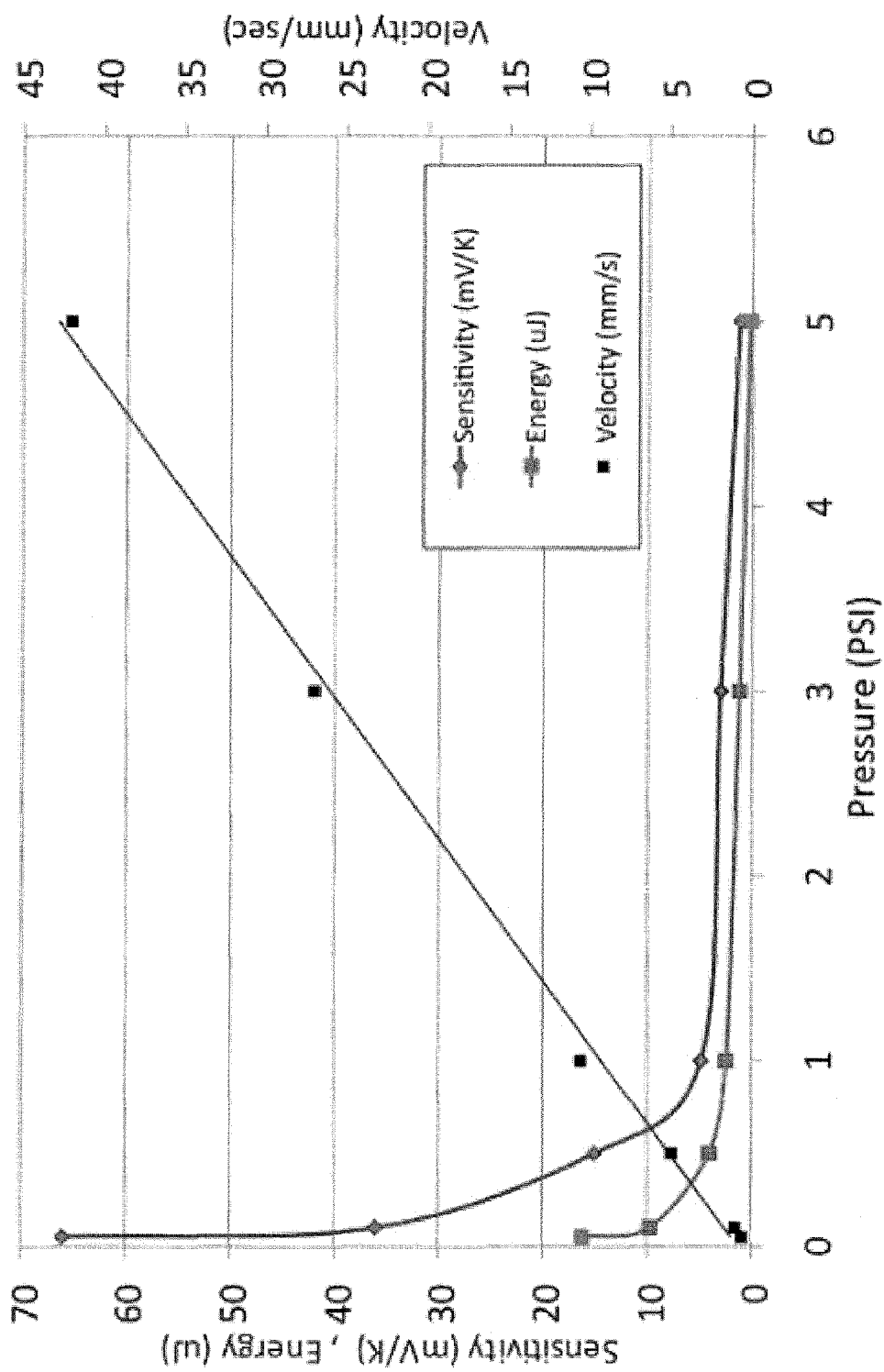
FIG. 11 depicts a graph relevant to flow rate selection based upon injection pressure, flow velocity vs. sensitivity and released energy, consistent with embodiments of the present disclosure.

FIG. 11 depicts a graph relevant to flow rate selection based upon injection pressure, flow velocity vs. sensitivity and released energy, consistent with embodiments of the present disclosure. For selection of flow rate, a number of different factors can be considered: a larger mixing area (more energy released) and higher density of active sensors in the chamber, the energy release from the reaction (proportional to mixing volume), flow velocity and calorimeter sensitivity versus the injection pressure at inlets. For lower pressure, the flow velocity was small, so the sample mixing and reaction time relied on diffusion of the samples, which can be time-consuming when compared to the convection transportation of sample to the reaction volume. On the other hand, high pressure and flow velocity results to a smaller mixing region, therefore smaller energy released, as well as a smaller number of active thermocouple sensors and thus lower sensitivity of the microfluidic calorimeter. In addition, the resolution of the device was limited by the rate of mixing within the chamber (after injection), which occurs primarily by diffusion. From the plot, a good pressure (rate) for the injection of the samples was found to be between 0.1 to 0.6 psi.

Figure 12:
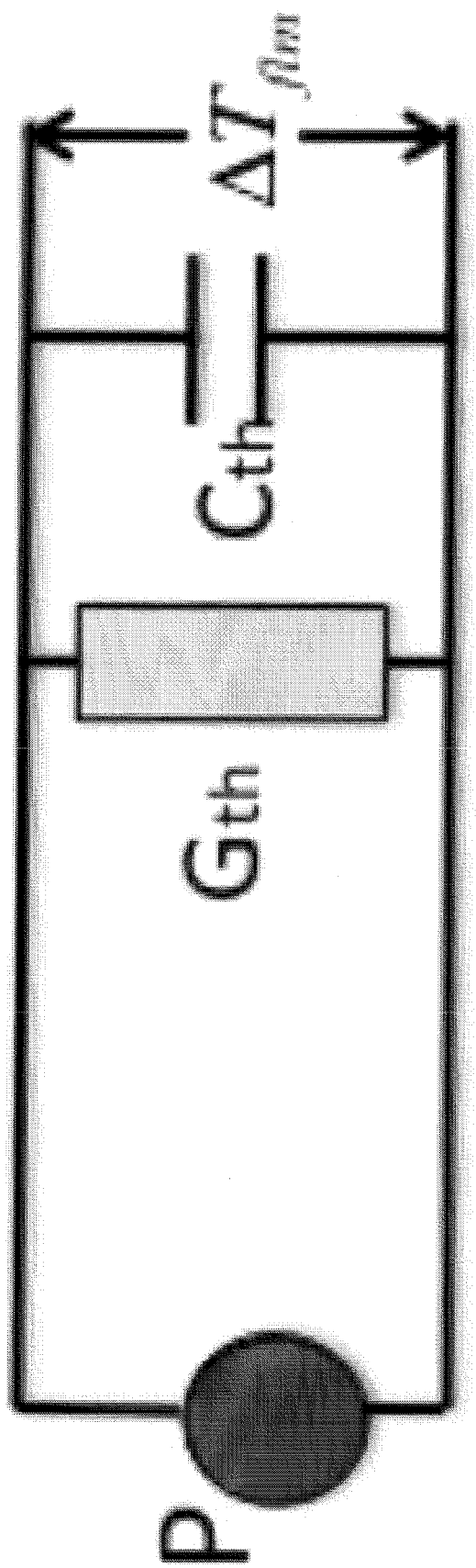
FIG. 12 depicts a thermal equivalent circuit of a calorimeter device, consistent with embodiments of the present disclosure.

Tests were carried out to characterize an experimental microfluidic calorimeter that used custom-made injector tubes to facilitate injection of sample media to the reaction chamber. To characterize the calorimeter, measurements were taken of the thermoelectric voltage induced in response to an electric power applied to a polysilicon-resistive heater in the center of chamber on a thin film SiN layer. The thermal equivalent circuit of the device can be thought of as a model depicted in FIG. 12, where P is the amplitude of applied power, Gth is the corresponding thermal conductance and Cth is the thermal capacitance of the device. Thermometer signal response to a step function power is predicted by $V(t)-S(P/G)(1-e^{-1/\tau})$ where $\tau$ is the thermal time constant. From the steady-state response, it was discovered that the experimental device had heat responsivity defined as voltage output (V) over applied heating power, of 39 V/W. The measured thermal conductance of the device, $G=S \cdot P/V$, is 9 $\mu$W/K under air condition.

The energy of a chemical reaction, which occurs in the chamber, is obtained as $E=t_m(t)/Sdt$. The time of measurement, $t_m$, is determined by the longer of either the time of the chemical reaction or the thermal relaxation time of the calorimeter. The chemical reaction time itself is a function of a single molecule reaction time, mixing time, synchronization and in case of enzymatic reaction (e.g., thermosequencing), multistep reactions. During these calibration runs, the measurement chamber is filled with deionized (DI) water. Together, the thermal conductance and the thermal time constant allow us to determine the device heat capacity, $C=G\tau$. The thermal time constant, $\tau=0.7$ s, is extracted from the measured rate of exponential growth in response to electrically induced heat steps. These data indicate the heat capacity of the water-filled device. It is believed that the amount of water contributes to the total heat capacity, so the intrinsic (empty) device heat capacity is believed to be ≈6.3 $\mu$J/K. During these calibrations and all other measurements performed, the integrated microfluidic calorimeter was enclosed in a box maintained at 25° C., with long-term temperature stability of 0.3° C. (over ≈3-h time period). Environmental temperature fluctuations had a negligible effect on the accuracy of the measurements because of the close proximity of the two ends of the thermocouple (≈400 um); the thermopiles only sense the temperature gradient between their two ends. Furthermore, the ends of the thermopiles are isolated from their environment by the air space.

Various other experimental results have suggested that particular embodiments of a microfluidic calorimeter provide 2 nW RMS in a 1 Hz band. The experiments include a test in which two silicon microchips are implemented side-by-side for differential operation. Thermal isolation of the reaction chamber was attained by using two freestanding 1.6 μm thin SiN membranes, encapsulated in air (or on-chip vacuum). Each membrane had a thermopile consisting of an array of 72 p- and n-doped polysilicon thermocouples and a polysilicon heater. Using two membranes resulted in higher power sensitivity of up to 84.7 V/W. The response time was less than 0.7 s.

The embodiments and specific applications discussed herein may be implemented in connection with one or more of the above-described aspects, embodiments and implementations, as well as with those shown in the figures and supported by the underlying provisional patent document, which is fully incorporated herein by reference.

The various embodiments as discussed herein may be implemented using a variety of structures and related operations/functions. For instance, one or more embodiments as described herein may be computer-implemented or computer-assisted, as by being coded as software within a coding system as memory-based codes or instructions executed by a logic circuit, computer processor, microprocessor, PC or mainframe computer. Such computer-based implementations are implemented using one or more programmable or programmed circuits that include at least one computer processor and internal/external memory and/or registers for data retention and access. One or more embodiments may also be implemented in various other forms of hardware, such as a state machine, programmed into a circuit such as a field-programmable gate array, or implemented using electronic circuits such as digital or analog circuits. In addition, various embodiments may be implemented using a tangible storage medium that stores instructions that, when executed by a processor, performs one or more of the steps, methods or processes described herein. These applications and embodiments may also be used in combination; for instance certain functions can be implemented using discrete logic (e.g., a digital or an analog circuit) that generates an output that is provided as an input to a processor. For instance, processing logic for processing and filtering sensor readings can be implemented using a combination of logic circuitry and a processing circuit configured using firmware or other software.

What is claimed is:

1. A method of measuring heat generated in a chemical reaction, the method comprising:
   providing a calorimeter sensor comprising:
      a substrate;
      a first integrated circuit device located on the substrate and including:
         a first microfluidic channel having a height of less than 1 mm from a first side to a second side,
         a first heat sensing circuit on the first side of the first channel, and
         a second heat sensing circuit on the second side of the first channel opposite the first side and facing the first heat sensing circuit; and
      a second integrated circuit device located on the substrate and proximal to the first device, the second device including:
         a second microfluidic channel having a height of less than 1 mm from a third side to a fourth side,
         a third heat sensing circuit on the third side of the second channel, and
         a fourth heat sensing circuit on the fourth side of the second channel opposite the third side and facing the third heat sensing circuit;
   providing a first and second different samples to the first microfluidic channel; and
   measuring heat generated from a reaction between the first and second samples using the first and second heat sensing circuits.

2. The method of claim 1, further comprising measuring heat of a reference sample in the second microfluidic channel.

3. The method of claim 2, further comprising:
   determining heat absorbed by the first integrated circuit device by comparing temperature readings of the first, second, third and fourth heat sensing circuits, and
   adding an amount of heat to the first microfluidic channel that is proportional to the heat absorbed by the first integrated circuit device.

4. The method of claim 1, wherein each of the first and second heat sensing circuits is a membrane having a plurality of p- and n-doped polysilicon thermocouples.

5. The method of claim 4, wherein the membrane includes a polysilicon heater arranged with the polysilicon thermocouples in a thermopile.

6. The method of claim 4, wherein the membranes are SiN membranes.

7. The method of claim 1, wherein the first and second heat sensing circuits are separated by 300 μM.

8. The method of claim 1, wherein providing the first and second samples to the first microfluidic channel of the first integrated circuit device includes injecting a controlled volume of the first and second samples into the first microfluidic channel by sequentially closing adjacent valves to facilitate peristaltic pumping of the first and second samples.

9. The method of claim 1, wherein the first and second samples are prepared with the same buffer solution.

10. A calorimeter sensor, comprising:
    a substrate;
    a first integrated circuit device located on the substrate and including
       a first microfluidic channel having a height of less than 1 mm from a first side to a second side,
       a first heat sensing circuit on the first side of the first channel, and
       a second heat sensing circuit on the second side of the channel opposite the first side and facing the first heat sensing circuit; and
    a second integrated circuit device located on the substrate and proximal to the first device, the second device including
       a second microfluidic channel having a height of less than 1 mm from a third side to a fourth side,
       a third heat sensing circuit on the third side of the second channel, and
       a fourth heat sensing circuit on the fourth side of the channel opposite the third side and facing the third heat sensing circuit.

11. The calorimeter sensor of claim 10, wherein the first and second sides are separated by no more than 300 μm.

12. The calorimeter sensor of claim 10, wherein each side is a SiN membrane.

13. The calorimeter sensor of claim 10, wherein each side has a thermopile including an array of p- and n-doped polysilicon thermocouples.

14. The calorimeter sensor of claim 13, wherein the thermopile includes a polysilicon heater.

15. The calorimeter sensor of claim 10, further comprising a respective set of valves coupled to a respective inlet of each microfluidic channel, the set of valves configured and arranged to facilitate peristaltic pumping of samples into the microfluidic channels.

16. The calorimeter sensor of claim 10, further including circuitry configured and arranged to filter first data that is received from the sensing circuits of the first device using a differential comparison of the first data to second data that is received from the sensing circuits of the second device.

17. The calorimeter sensor of claim 10, wherein each side is a SiN membrane separated from external heat by one of an air gap and a vacuum gap.

18. The calorimeter sensor of claim 10, wherein the calorimeter sensor further includes a plurality of beads encapsulated in the first channel, wherein each bead is coated with a plurality of DNA strands.

* * * * *